United States Patent
Maruyama et al.

(10) Patent No.: US 6,664,063 B1
(45) Date of Patent: Dec. 16, 2003

(54) METHODS FOR SEPARATING, FRACTIONATING AND ANALYZING GENE OF VIRUS EXISTING IN HYDROSPHERE

(75) Inventors: Akihiko Maruyama, Ibaraki (JP); Hisaaki Yagi, Ibaraki (JP); Ryuichiro Kurane, Chiba (JP)

(73) Assignee: National Institute of Advanced Industrial Science and Technology (JP)

( * ) Notice: Subject to any disclaimer, the term of this patent is extended or adjusted under 35 U.S.C. 154(b) by 0 days.

(21) Appl. No.: 09/979,503

(22) PCT Filed: May 29, 2000

(86) PCT No.: PCT/JP00/01968
§ 371 (c)(1),
(2), (4) Date: Nov. 23, 2001

(87) PCT Pub. No.: WO00/71700
PCT Pub. Date: Nov. 30, 2000

(30) Foreign Application Priority Data

May 25, 1999 (JP) .......................................... 11-145341

(51) Int. Cl.$^7$ .............................. C12Q 1/68; C12Q 1/70
(52) U.S. Cl. ................................................. 435/6; 435/5
(58) Field of Search .......................................... 435/5, 6

(56) References Cited

U.S. PATENT DOCUMENTS 4,695,548 A 9/1987 Cantor et al.
5,457,050 A 10/1995 Mazurek

FOREIGN PATENT DOCUMENTS

| JP | 63-159394 | 7/1988 |
| JP | 7-163352 | 6/1995 |
| JP | 9-94098 | 4/1997 |

OTHER PUBLICATIONS

Bergh et al., Aug. 10, 1989, "High abundance of viruses found in aquatic environments," Nature 340(6233): 467–468.

Luria et al., 1978, "The Biochemistry of Viruses," in *General Virology*, 3$^{rd\ edition}$, John Wiley and Sons, Inc., pp. 106–107.

Rochelle et al., Dec. 1991, "A Simple Technique for Electroelution of DNA from Environmental Samples," BioTechniques 11(6): 724, 726–728.

Schwartz et al., May 1, 1984, "Separation of Yeast Chromosome–Sized DNAs by Pulse Field Gradient Gel Electrophoresis," Cell 37(1): 67–75.

Communication and Supplementary European Search Report for application EP00912929, mailed on Jul. 9, 2002 (4 pages).

*Primary Examiner*—Hankyel T. Park
(74) *Attorney, Agent, or Firm*—Finnegan, Henderson, Farabow, Garrett & Dunner, L.L.P.

(57) ABSTRACT

A method for separating genes from viruses existing in hydrosphere in an intact state, a method for fractionating thus separated genes, and a method for analyzing thus fractionated genes.

15 Claims, 5 Drawing Sheets

US 6,664,063 B1

METHODS FOR SEPARATING, FRACTIONATING AND ANALYZING GENE OF VIRUS EXISTING IN HYDROSPHERE

FIELD OF THE INVENTION

The present invention relates to a method for separating genes from viruses existing in hydrosphere in an intact state, a method for fractionating thus separated genes, and a method for analyzing thus fractionated genes.

BACKGROUND ART

In 1989, Bergh et al. reported the existence of an enormous number of virus-like particles in hydrosphere, such as lake water and seawater as a result of their observation using an electron microscope [Bergh et al.: Nature 340:467–468 (1989)]. In general, it is difficult to discriminate viruses from one another, which are similar in form, by the observation of viruses with an electron microscope. A method is known wherein a viral coat is broken with the aid of a surfactant and/or a proteolytic enzyme to analyze released genes. However, chains of genes, which are released in a solution, are often broken by, for example, mechanical shearing force, and it is difficult to separate genes in an intact state. When performing gene analysis, it is difficult to analyze entire viruses because, unlike prokaryotes or eukaryotes, common gene sequences have not been known. A general separation method, by concentration using polyethylene glycol, results in differences in viruses which precipitate depending on its concentration. Therefore, there is a limit on the analysis of every kinds of viruses in hydrosphere in this method.

SUMMARY OF THE INVENTION

The object of the present invention is to provide a method for separating genes from viruses existing in hydrosphere in an intact state, a method for fractionating thus separated genes, and a method for analyzing thus fractionated genes.

We had keenly studied in order to attain the above object and found that virus DNA could be separated in an intact form by performing ultracentrifugation to concentrate virus particles in water samples, embedding the virus particles in a gel, followed by treating with a proteolytic enzyme and/or a surfactant. This led to the completion of the present invention.

Specifically, the present invention provides a method for separating virus genes comprising the steps of:
 (a) separating virus particles from hydrosphere;
 (b) embedding the virus particles obtained in step (a) in a gel; and
 (c) treating the embedded product obtained in step (b) with a proteolytic enzyme and/or a surfactant.

The present invention further provides a method for fractionating virus genes comprising the steps of:
 (a) separating virus particles from hydrosphere;
 (b) embedding the virus particles obtained in step (a) in a gel;
 (c) treating the embedded product obtained in step (b) with a proteolytic enzyme and/or a surfactant; and
 (d) performing electrophoresis on the proteolytic enzyme- and/or surfactant-treated product obtained in step (c).

Furthermore, the present invention provides a method for analyzing virus genes comprising the steps of:
 (a) separating virus particles from hydrosphere;
 (b) embedding the virus particles obtained in step (a) in a gel;
 (c) treating the embedded product obtained in step (b) with a proteolytic enzyme and/or a surfactant;
 (d) performing electrophoresis on the proteolytic enzyme- and/or surfactant-treated product obtained in step (c); and
 (e) extracting genes from the electrophoresis gel obtained in step (d) to analyze the genes.

The present invention will be described in more detail as follows.

FIG. 1 shows an embodiment of methods according to the present invention for separating, fractionating, and analyzing virus genes existing in hydrosphere. At the outset, virus particles, existing in sample water obtained from hydrosphere, are separated (step A). Subsequently, the virus particles thus obtained are embedded in a gel (step B). The embedded product is then treated with proteinase K, SDS or the like to decompose viral coats (step C), followed by the fractionation of virus genes (step D). Finally, the fractionated genes are analyzed by Southern blot analysis or Northern blot analysis (step E). More specifically, such intact separation of virus genes can be carried out as follows.

1. Separating Virus Genes from Hydrosphere
(1) Collecting Sample Water Containing Virus Particles From Water "Hydrosphere" refers to all aqueous environments including natural and artificial aqueous environments that could contain virus particles. For instance, a natural aqueous environment includes seas, lakes, and rivers. An artificial aqueous environment includes, but is not limited to, a culture solution, active sludge, wastewater, and blood. Sample water containing virus particles includes those derived from the above hydrosphere. For instance, sample water can be collected by recovering a water sample from a desired depth in seas and lakes onto a ship or onto land using Niskin water sampler, Bandon water sampler, and so on.
(2) Removing Impurities From Sample Containing Virus Particles Various organisms as shown in FIG. 2 generally exist in seawater, lake water, and river water. The method of the present invention is directed to virus particles existing in these waters (hydrosphere).

In order to separate virus particles from sample water, impurities are first removed from sample water obtained in (1) above. Impurities can be removed by, for example, low speed centrifugation and/or filtration. Here, "impurities" refer to relatively large sample water components, for example, soil particles, clay mineral, fraction of animal tissue and plant texture, phytoplankton and zooplankton, and detritus. Preferably, low speed centrifugation is carried out at about 6,000×g for 10 to 15 min. Centrifuges that can be used for low speed centrifugation include Model HP-30 manufactured by Beckman and Model CR 26H manufactured by Hitachi, Ltd. Further, when impurities are removed by filtering a sample solution, filter paper (for example, No. 3 manufactured by WATT MANN CO,. LTD) may be used. When sample water is limpid, the step of low speed centrifugation may be omitted.
(3) Purifying Virus Particles Purification of virus particles from the impurities-removed solution obtained in (2) above can be carried out by filtration. Filters that can be used for purification of viruses include those having pores with a diameter of 0.1 to 0.45 $\mu$m, preferably 0.20 to 0.22 $\mu$m. For example, hydrophilic polyvinylidene difluoride membrane having a pore diameter of 0.22 $\mu$m (Model GVWP manufactured by Millipore) may be used. Pore diameter may be properly selected according to the size of organisms to be removed by filtration, for example, referring to FIG. 3. In general, most bacteria living in water can be removed by using a filter having a pore diameter of 0.20 to 0.22 μm. Filter materials include hydrophilic polyvinylidene difluoride (PVDF), hydrophilic polytetrafluoroethylene (PTFE), and polycarbonate, having low absorption to protein. In order to perform filtration in a more rapid manner, in filtration, pressure is preferably applied. For example, filtration pressure is not more than 100 mmHg, preferably not more than 30 mmHg.

(4) Separating Virus Particles

Virus particles from the filtrate obtained in (3) above can be separated by precipitating virus particles by ultracentrifugation. Ultracentrifugation is preferably carried out at 100,000 to 130,000×g for 3 to 16 hr. Centrifuges that can be used for ultracentrifugation include Model CP 90α manufactured by Hitachi, Ltd and Optima XL-100K manufactured by Beckman.

(5) Treating With Nuclease

The precipitate of virus particles obtained in (4) above sometimes contains a large quantity of naked nucleic acids, and nucleic acids absorbed and held on inorganic particles and detritus, which are derived from other organisms. These nucleic acids can be removed by treating them with nuclease. DNase is used to decompose DNA and RNase is used to decompose RNA. That is, the virus precipitate obtained in (4) above is suspended, for example, in a TM buffer or TE buffer to incubate with a proper amount of DNase or RNase. Adding an EDTA solution, an RNasin solution and the like can stop the reaction. In this way, a suspension of virus particles can be obtained which contains no naked nucleic acids therein.

2. Embedding Virus Particles in a Gel

In separating genes from virus particles, a treatment with a proteolytic enzyme and/or a surfactant with virus particles suspended in a liquid often results in breakage of genes by physical shearing force over the course of treatment. Therefore, virus particles are immobilized by embedding them in a gel. The immobilized virus particles are treated with a proteolytic enzyme or a surfactant. This can prevent the breakage of genes. Embedding virus particles in the gel can be carried out by adding a gelling agent, for example a low-melting point agarose, to a virus suspension. That is, the nuclease treated virus suspension obtained in 1 above is heated to a temperature at which the low-melting point agarose does not solidify (for example 55° C.). A gelling agent, for example, a low-melting point agarose is then added thereto, followed by thorough mixing and cooling to solidification. The final concentration of the agarose is preferably about 1%.

3. Decomposing Virus Coat

The coats of virus particles embedded in the gel in 2 above can be decomposed and removed by treating a gel embedded product with a virus coat decomposing solution containing, for example, a proteolytic enzyme and/or a surfactant. Proteolytic enzymes that can be used herein include proteinase K (manufactured by NIPPON GENE CO., LTD.). Surfactants that can be used herein include sodium dodecyl sulfate (SDS). The decomposition of the virus coat can be accomplished by thorough permeation of the proteolytic enzyme and/or the surfactant into a gel.

4. Fractionating and Detecting Virus Genes by Electrophoresis

The product of virus coat decomposition obtained in 3 above is subjected to electrophoresis (for example pulsed-field gel electrophoresis), thereby fractionating nucleotides contained in the treated product by size. That is, gel, which has been subjected to virus coat decomposition, is sliced into a size small enough to fit in a well. The sliced gel is then applied to an electrophoresis gel having agarose or the like as a carrier. Subsequently, under pulsed-field gel electrophoresis conditions corresponding to fractionated size range, virus genes can be fractionated by size. The fractionated virus genes can be detected with the aid of a nucleic acid stainer or the like. Also, the separation of virus and a quantitative purification and fractionation of genes thereof enables the investigation of quantitative ratio of each size existing therein.

5. Analyzing Virus Genes

The virus genes fractionated in 4 above can be analyzed, for example, by Southern blot analysis or Western blot analysis. When the size of fractionated genes is large, cleaving of a nucleotide chain to some extent prior to blotting can enhance the blotting efficiency. Treating the fractionated gel with ultraviolet or a hydrochloric acid can cleave the nucleotide chain. The blotted genes can be analyzed in accordance with conventional methods regarding, for example, existence and quantity of specific genes by hybridization using a labeled probe. For example, when analyzing virus genes from a sample water collected from a sea area where a harmful red tide is likely to occur, a synthetic probe may be provided in accordance with the nucleotide sequence of genes of viruses associated with the decrease and increase of plankton causative of the red tide (for example, Chattonella virus) in order to investigate the existence, the quantity, and the like of the viruses.

BEST MODE TO CARRY OUT THE INVENTION

The present invention will be described in more detail with reference to the following examples, though these examples are not to be construed as limiting the scope of the present invention.

Example 1 Separating Virus Particles From Seawater and Lake Water

Figure 1:
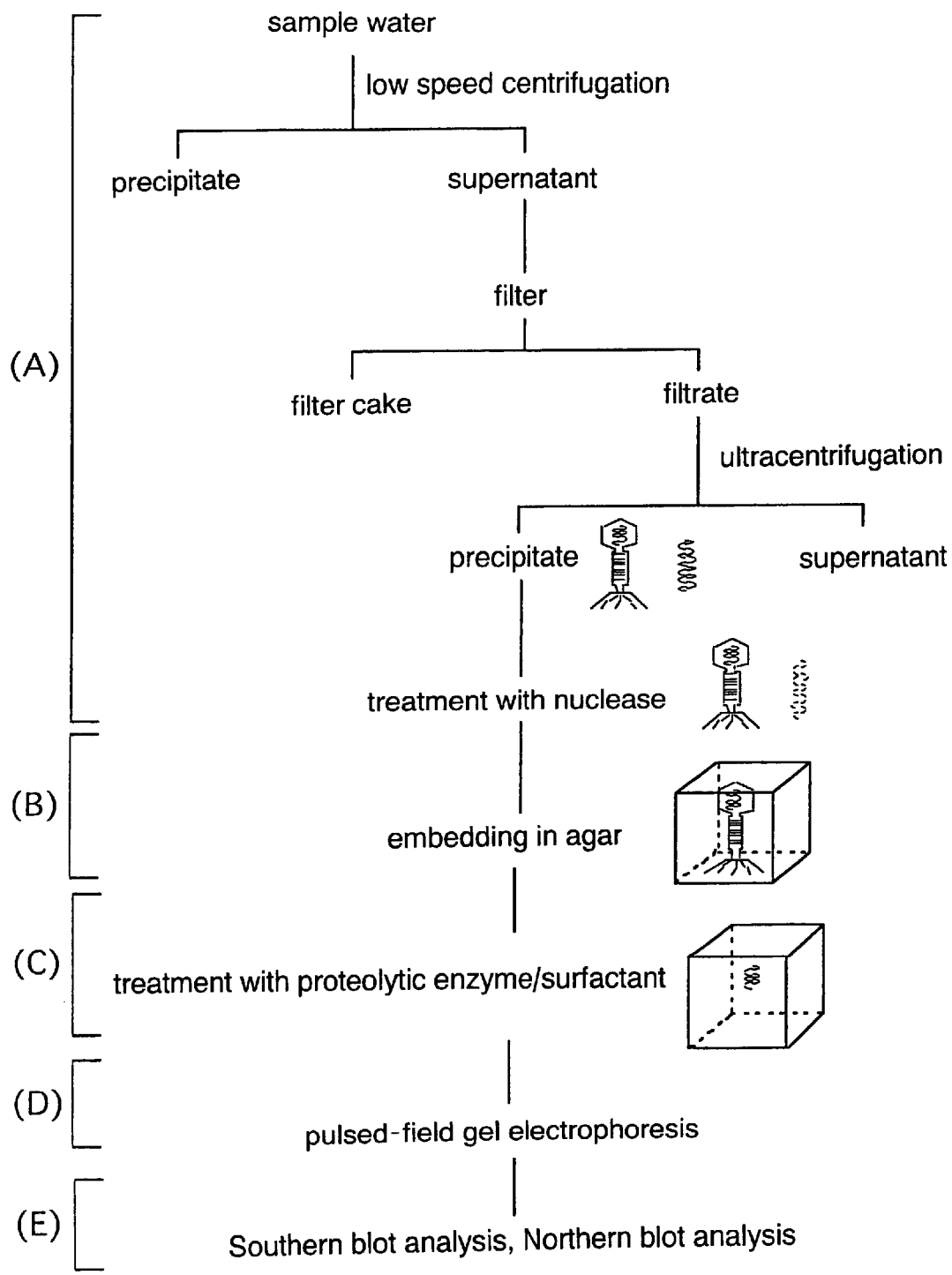
FIG. 1 shows a separation method of virus genes according to the present invention.
Figure 2:
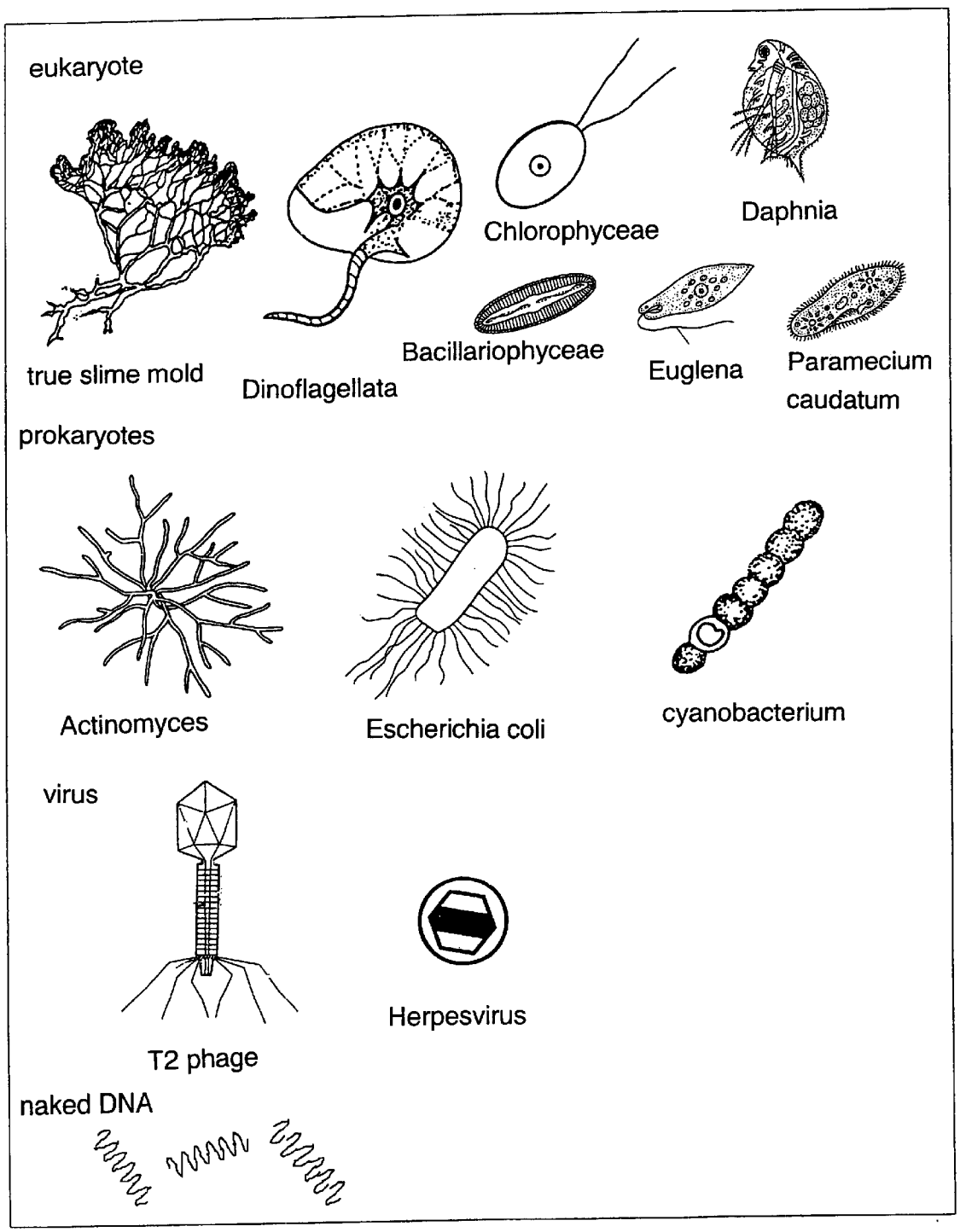
FIG. 2 shows the form of microorganisms and the like contained in lake water and seawater.
Figure 3:
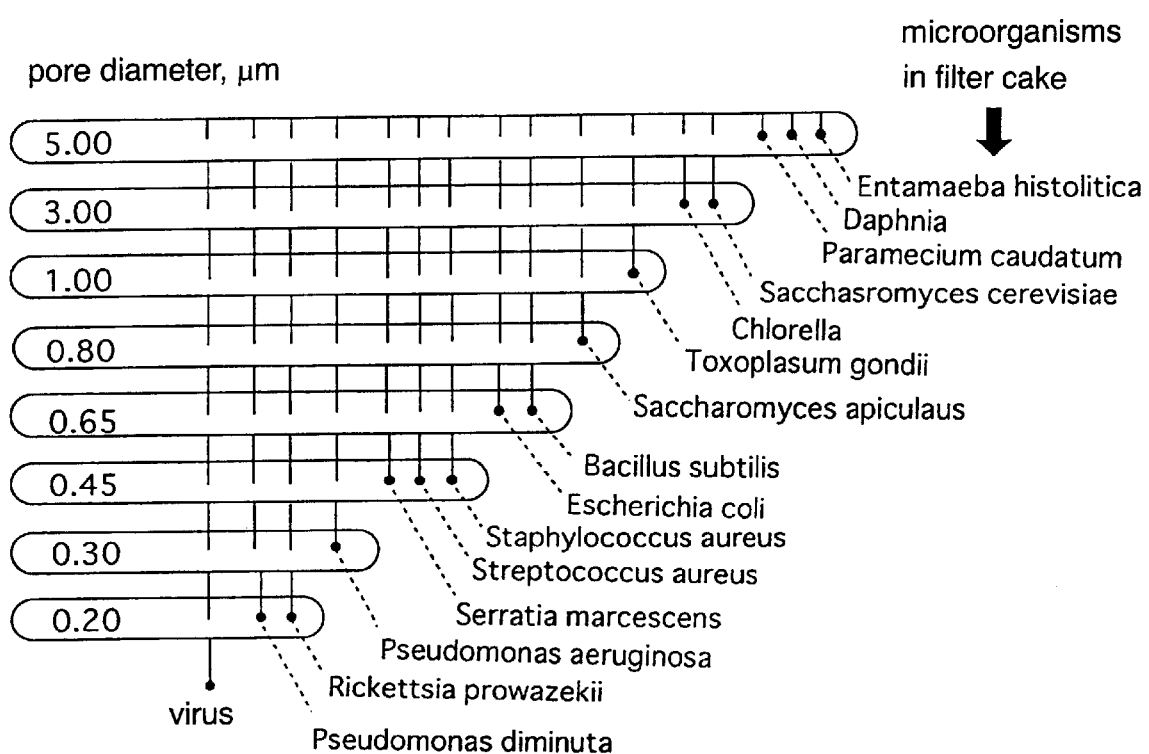
FIG. 3 shows the relationship between pore diameter of a filter and microorganisms removable therewith.
Figure 4:
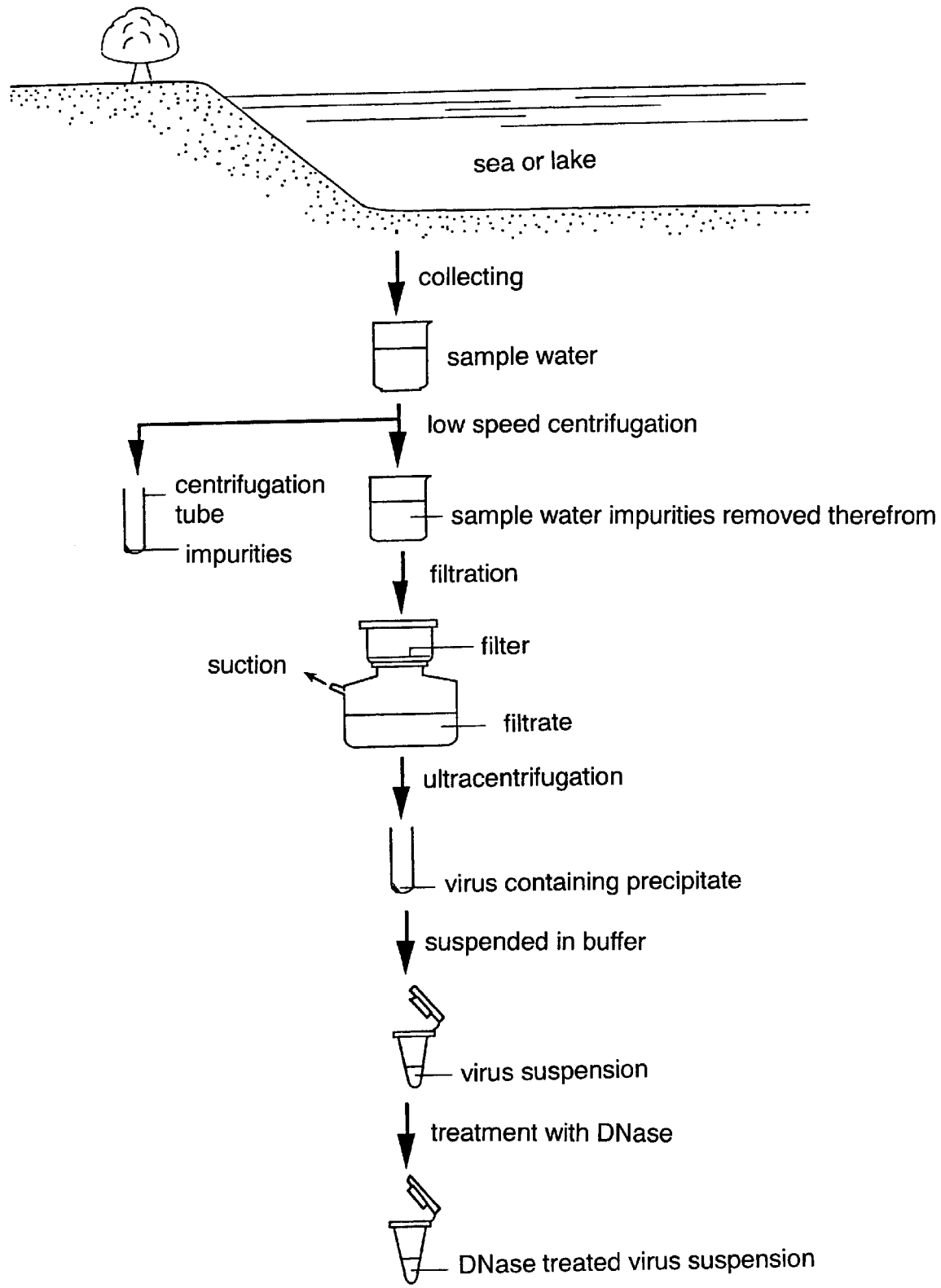
FIG. 4 shows a separation method of a virus from water.

In accordance with the procedure shown in FIG. 4, virus particles were separated from sample water collected from Tokyo Bay and Kasumigaura. Specifically, 500 ml of sample water was first centrifuged using a centrifuge equipped with an angle rotor (Model KR 200A manufactured by KUBOTA CORPORATION) at 6,000×g for 10 min to remove impurities precipitated. Subsequently, the resultant supernatant was subjected to suction filtration with a PVDF membrane filter having a pore diameter of 0.22 μm (manufactured by IWAKI&CO., LTD). The resultant filtrate was subjected to ultracentrifugation with a centrifuge (Model CP 90α manufactured by Hitachi, Ltd) at 125,000×g for 3 hr. The precipitate was dissolved in 0.5 to 1.0 ml of TM buffer (10 mM Tris-10 mM $MgCl_2$ (pH 7.5)) to prepare a virus solution. To the thus obtained solution (450 μl) was added DNase to a final concentration of 25 μg/ml. The mixture was incubated at 37° C. for 30 min to digest naked DNA. 50 μl of 500 mM EDTA (pH 8.2) was then added thereto in order to terminate the DNase reaction.

Example 2 Separating Virus Genes

Genes were separated from virus particles obtained in Example 1. To the virus particle-containing solution heated to 55° C. was added an equal volume of 2% low-melting point agarose (55° C., heat dissolved, Agarose GB manufactured by NIPPON GENE CO., LTD.). The mixture was poured into a cast to solidify. The solidified virus embedded product was transferred to a sterilized tube and treated with a virus coat decomposing solution (1 mg/ml proteinase K, 1% SDS, 0.5 M EDTA (pH 8.2)) at 55° C. for 15 to 18 hr. The virus embedded product was then rinsed with a TE buffer (10 mM Tris-HCl, 1 mM EDTA (pH 8.0)), and immersed in the TE buffer and stored at 4° C.

Example 3 Pulsed-Field Gel Electrophoresis of Virus DNA

Virus DNA was subjected to a pulsed-field gel electrophoresis with CHEF Mapper System (manufactured by Bio-Rad) to fractionate the virus DNA. That is, the virus embedded product obtained in Example 2 was thinly sliced. Each slice was measured for its weight on a wet basis, and applied to a previously prepared 1% agarose gel. Subsequently, electrophoresis was conducted at an initial switching time of 0.06 sec and a final switching time of 17.33 sec, at a voltage of 6 V/cm, for a migration time of 7 hr 53 min. After electrophresis, the product was stained with SYBR (SYBR Green) for 60 to 120 min.

Figure 5:
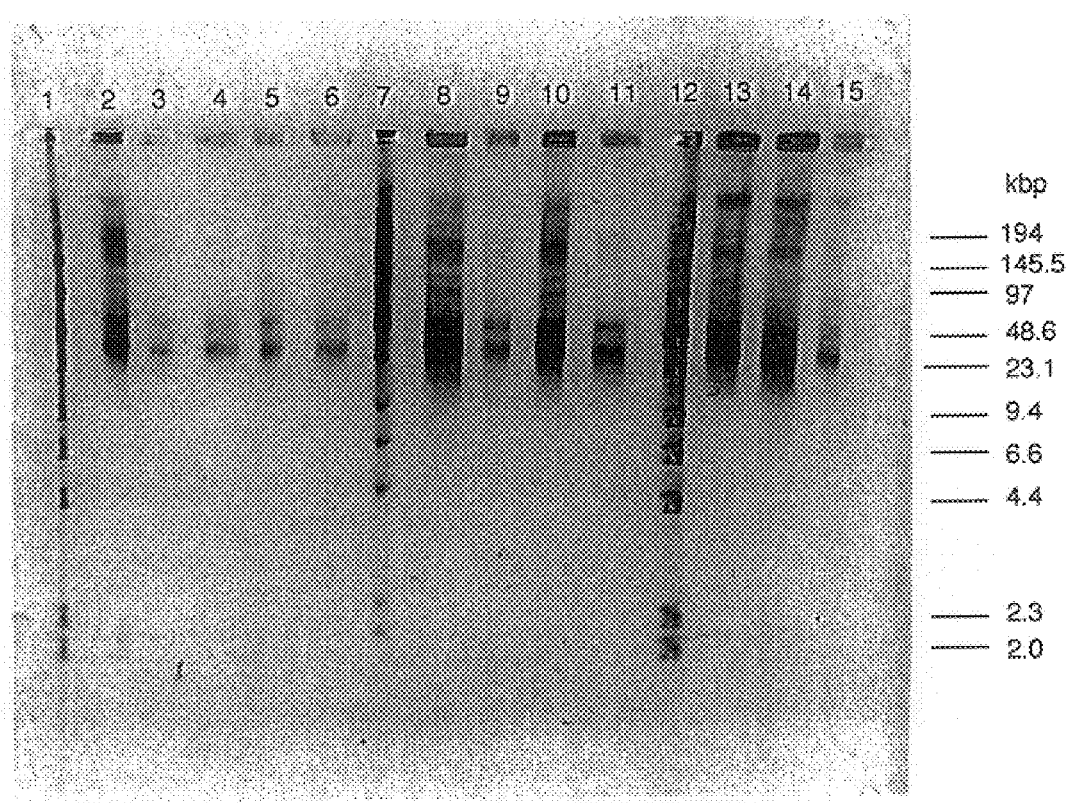
FIG. 5 shows a photograph of pulsed-field gel electrophoresis conducted for virus genes separated from seawater and lake water in accordance with the method of the present invention.

FIG. 5 shows a stained gel. In FIG. 5, each of lanes 1, 7, and 12 represents a migrated DNA size marker. For other lanes, lane 2 is a result of sample water collected from Tokyo Bay on Sep. 24, 1997, lanes 3 to 6 are results of sample water collected from Tokyo Bay on Mar. 18, 1998. Among them, lane 3 shows a case wherein the sample water was collected from sea level of water-collection point T1; lane 4, 15 m below sea level of point T1; lane 5, sea level of water-collection point T2; and lane 6, 20 m below sea level of point T2. Lanes 8 to 11 are results of sample water collected from Tokyo Bay on Aug. 19, 1998. Among them, lane 8 shows a case using sample water collected from sea level of water-collection point T1; lane 9, 15 m below sea level of point T1; lane 10, sea level of water-collection point T2; and lane 11, 20 m below sea level of point T2. Further, lanes 13 to 15 are results of sample water collected from Kasumigaura. Among them, lane 13 shows a case using sample water collected on May 19, 1998; lane 14, on Jun. 17, 1998; and lane 15, on Jul. 14, 1998. As is apparent from FIG. 5, DNA, which has a molecular size exceeding 30 kbp and is considered to contain intact virus genes, has been fractionated.

INDUSTRIAL APPLICABILITY

The present invention provides methods for separating, fractionating, and analyzing virus genes existing in hydrosphere in an intact state. The present invention is useful for an identification of kinds of viruses existing in hydrosphere and for an estimate of a quantitative ratio of viruses existing in hydrosphere.

What is claimed is:

1. A method for separating virus genes, comprising:
   (a) separating virus particles from hydrosphere;
   (b) embedding the virus particles obtained in (a) in a gel; and
   (c) treating the embedded product obtained in (b) with a proteolytic enzyme and/or a surfactant.

2. A method for analyzing virus genes, comprising:
   (a) separating virus particles from hydrosphere;
   (b) embedding the virus particles obtained in (a) in a gel;
   (c) treating the embedded product obtained in (b) with a proteolytic enzyme and/or a surfactant; and
   (d) subjecting the proteolytic enzyme- and/or sufactant-treated product obtained in (c) to electrophoresis.

3. A method for analyzing virus genes, comprising:
   (a) separating virus particles from hydrosphere;
   (b) embedding the virus particles obtained in (a) in a gel;
   (c) treating the embedded product obtained in (b) with a proteolytic enzyme and/or a surfactant;
   (d) subjecting the proteolytic enzyme- and/or sufactant-treated product obtained in (c) to electrophoresis; and
   (e) analyzing the electrophoresis gel obtained in step (d).

4. The method according to claim 1, wherein separating the virus particles comprises using a filter having a pore diameter of 0.1 to 0.45 μm.

5. The method according to claim 1, wherein separating the virus particles comprises an ultracentrifugation.

6. The method according to claim 1, wherein separating the virus particles comprises using a filter having a pore diameter of 0.1 to 0.45 μm and an ultracentrifugation.

7. The method according to claim 1 or 6, wherein separating the virus particles comprises treating with a nuclease.

8. The method according to claim 2, wherein separating the virus particles comprises using a filter having a pore diameter of 0.1 to 0.45 μm.

9. The method according to claim 2, wherein separating the virus particles comprises an ultracentrifugation.

10. The method according to claim 2, wherein separating the virus particles comprises using a filter having a pore diameter of 0.1 to 0.45 μm and an ultracentrifugation.

11. The method according to claim 2 or 10, wherein separating the virus particles comprises treating with a nuclease.

12. The method according to claim 3, wherein separating the virus particles comprises using a filter having a pore diameter of 0.1 to 0.45 μm.

13. The method according to claim 3, wherein separating the virus particles comprises an ultracentrifugation.

14. The method according to claim 3, wherein separating the virus particles comprises using a filter having a pore diameter of 0.1 to 0.45 μm and an ultracentrifugation.

15. The method according to claim 3 or 14, wherein separating the virus particles comprises treating with a nuclease.

* * * * *

UNITED STATES PATENT AND TRADEMARK OFFICE
CERTIFICATE OF CORRECTION

PATENT NO. : 6,664,063 B1
DATED : December 16, 2003
INVENTOR(S) : Akihiko Maruyama et al.

It is certified that error appears in the above-identified patent and that said Letters Patent is hereby corrected as shown below:

<u>Title page,</u>
Item [22], PCT filing date, "May 29, 2000" should read -- March 29, 2000 --.

<u>Column 6,</u>
Lines 20 and 28, "sufactant-" should read -- surfactant- --.

Signed and Sealed this

Twenty-seventh Day of April, 2004

JON W. DUDAS
*Acting Director of the United States Patent and Trademark Office*